(12) United States Patent
Duchoslav et al.

(10) Patent No.: US 10,825,669 B2
(45) Date of Patent: Nov. 3, 2020

(54) METHOD FOR PROPOSAL OF COMPOUND ANALOG STRUCTURES USING ACCURATE PRODUCT ION SPECTRA

(71) Applicant: DH TECHNOLOGIES DEVELOPMENT PTE. LTD., Singapore (SG)

(72) Inventors: Eva Duchoslav, Toronto (CA); Pui Yee Iris Shek, Richmond Hill (CA); Alina Dindyal-Popescu, Maple (CA)

(73) Assignee: DH Technologies Development Pte. Ltd., Singapore (SG)

(*) Notice: Subject to any disclaimer, the term of this patent is extended or adjusted under 35 U.S.C. 154(b) by 333 days.

(21) Appl. No.: 15/851,823

(22) Filed: Dec. 22, 2017

(65) Prior Publication Data
US 2018/0190480 A1  Jul. 5, 2018

Related U.S. Application Data

(60) Provisional application No. 62/440,963, filed on Dec. 30, 2016.

(51) Int. Cl.
*H01J 49/00* (2006.01)
*G01N 33/50* (2006.01)
(Continued)

(52) U.S. Cl.
CPC .......... *H01J 49/0036* (2013.01); *G01N 33/50* (2013.01); *G01N 33/94* (2013.01);
(Continued)

(58) Field of Classification Search
CPC .................................................. H01J 49/0036
(Continued)

(56) References Cited

U.S. PATENT DOCUMENTS

| 2007/0023633 A1* | 2/2007 | Wang ...................... H01J 49/02 250/282 |
| 2012/0108448 A1* | 5/2012 | Kuhlmann .......... H01J 49/0036 506/8 |

OTHER PUBLICATIONS

Tiller et al. "High-throughput, accurate mass liquid chromatography/tandem mass spectrometry on a quadrupole time-of-flight system as a 'first-line' approach for metabolite identification studies" Rapid Commun. Mass Spectrom. 2008; 22: 1053-1061 (Year: 2008).*

(Continued)

*Primary Examiner* — Christine T Mui
*Assistant Examiner* — Emily R. Berkeley
(74) *Attorney, Agent, or Firm* — John R. Kasha; Kelly L. Kasha; Kasha Law LLC

(57) ABSTRACT

A metabolized product ion spectrum is produced for a metabolized version of a known compound using tandem mass spectrometry. Metabolized structures are inferred from the metabolized product ion spectrum. An unmetabolized product ion spectrum is received for an unmetabolized version of the known compound and unmetabolized structures are inferred from the unmetabolized product ion spectrum. Each of the metabolized structures is compared to the unmetabolized structures, producing matched and unmatched structures. For each unmatched structure, a biotransformation repository is searched for modifications and each unmatched structure and the modifications found are again compared to the unmetabolized structures, producing modified matched structures. For each atomic index of the known compound, an unmodified specificity is calculated from the matched structures, a modified intensity specificity is calculated from the modified matched structures, and a score is calculated from the specificities. Atomic indices with the highest score are identified as sites of modification.

3 Claims, 11 Drawing Sheets

(51) Int. Cl.
    *G01N 33/94*     (2006.01)
    *G16C 99/00*     (2019.01)
    *G16C 20/20*     (2019.01)

(52) U.S. Cl.
    CPC ............. *G16C 20/20* (2019.02); *G16C 99/00* (2019.02); *G01N 2560/00* (2013.01); *H01J 49/004* (2013.01)

(58) Field of Classification Search
    USPC .......................................................... 436/173
    See application file for complete search history.

(56) References Cited

OTHER PUBLICATIONS

Herebian et al. "Identification of NTBC metabolites in urine from patients with hereditary tyrosinemia type 1 using two different mass spectrometric platforms: triple stage quadrupole and LTQ-Orbitrap" Rapid Commun. Mass Spectrom. 2010; 24: 791-800 (Year: 2010).*

\* cited by examiner

| # | Mass (m/z) | Ion Formula | Intensity (cps) | Proposed Structures | Score | NL/fragment scores (> 90% of highest score) | Atom indices (Taken from Parent Atoms) |
|---|---|---|---|---|---|---|---|
| 1 | 57.0357 | C3H5O | 8144 | 3 | 36 | 47 | 7,8,9,11 |
| | | | | | | 43.5 | 4,7,8,9 |
| | | | | | | 43.5 | 1,7,8,9 |
| 2 | 62.0265 | CH4NO2 | 5555 | 1 | 40.5 | 51.5 | 0,2,4,6 |
| 3 | 65.041 | C5H5 | 1259 | 0 | 3 | 33.5 | 3,12,13,15,16 |
| | | | | | | 33.5 | 5,12,13,15,16 |
| | | | | | | 47.5 | 4,7,8,9,11 |
| | | | | | | 47.5 | 1,7,8,9,11 |
| 4 | 75.0459 | C3H7O2 | 2041 | 4 | 36.5 | 43 | 1,4,7,8,9 |
| 5 | 77.0404 | C6H5 | 4816 | 1 | 36.5 | 47.5 | 3,5,12,13,15,16 |
| 6 | 79.0559 | C6H7 | 2283 | 1 | 36.5 | 47.5 | 3,5,12,13,15,16 |
| 7 | 91.0553 | C7H7 | 3484 | 0 | 3 | | |
| 8 | 93.0347 | C6H5O | 4885 | 2 | 36.5 | 47.5 | 1,3,5,12,13,15,16 |
| | | | | | | 47.5 | 3,5,10,12,13,15,16 |
| 9 | 93.0704 | C7H9 | 772 | 0 | 3 | | |
| 10 | 95.0502 | C6H7O | 3544 | 2 | 36.5 | 47.5 | 1,3,5,12,13,15,16 |
| | | | | | | 47.5 | 3,5,10,12,13,15,16 |
| 11 | 103.0552 | C8H7 | 6008 | 0 | 3 | | |
| 12 | 105.0709 | C8H9 | 5395 | 0 | 3 | | |
| 13 | 107.0497 | C7H7O | 1593 | 2 | 40 | 51 | 3,5,10,12,13,14,15,16 |
| 14 | 109.0292 | C6H5O2 | 519 | 1 | 36.5 | 47.5 | 1,3,5,10,12,13,15,16 |
| 15 | 110.0371 | C6H6O2 | 4255 | 1 | 33.5 | 44.5 | 1,3,5,10,12,13,15,16 |
| 16 | 115.0547 | C9H7 | 488 | 0 | 3 | | |
| 17 | 118.0605 | C4H8NO3 | 15553 | 2 | 40 | 51 | 0,2,4,6,7,8,9,11 |
| | | | | | | 47.5 | 0,1,2,4,6,7,8,9 |
| 18 | 120.0574 | C8H8O | 1632 | 1 | 36.5 | 37.5 | 7,8,1,3,5,13,15,16,12 |
| 19 | 121.0291 | C7H5O2 | 3948 | 2 | 37 | 48 | 1,3,5,10,12,13,14,15,16 |
| | | | | | | 44 | 1,3,5,8,10,12,13,15,16 |
| 20 | 121.0647 | C8H9O | 2141 | 1 | 34.5 | | |
| 21 | 122.0368 | C7H6O2 | 10426 | 2 | 37 | 48 | 1,3,5,10,12,13,14,15,16 |
| 22 | 125.0603 | C7H9O2 | 6022 | 2 | 40.5 | 51.5 | 1,3,5,10,12,13,15,16 |
| 23 | 131.0491 | C9H7O | 1199 | 1 | 37 | 48 | 1,3,5,7,8,9,12,13,15,16 |
| 24 | 135.0808 | C9H11O | 5015 | 1 | 37.5 | 48.5 | 1,3,5,7,8,9,12,13,15,16 |
| 25 | 137.0599 | C8H9O2 | 2103 | 3 | 42 | 53 | 1,3,5,8,10,12,13,14,15,16 |
| | | | | | | 49.5 | 1,3,5,7,8,11,12,13,15,16 |
| 26 | 145.0648 | C10H9O | 641 | 0 | 8 | | |
| | | | | | | 49 | 1,3,5,7,8,9,11,12,13,15,16 |
| | | | | | | 46 | 1,3,5,7,8,10,12,13,14,15,16 |
| | | | | | | 45.5 | 1,3,4,5,7,8,9,12,13,15,16 |
| 27 | 148.052 | C9H8O2 | 2070 | 4 | 38 | 45.5 | 1,3,5,7,8,9,10,12,13,15,16 |
| | | | | | | 52.5 | 1,3,5,7,8,9,11,12,13,15,16 |
| | | | | | | 49.5 | 1,3,5,7,8,10,12,13,14,15,16 |
| | | | | | | 48.5 | 1,3,4,5,7,8,9,12,13,15,16 |
| 28 | 151.0756 | C9H11O2 | 2635 | 4 | 41.5 | 46.5 | 1,3,5,7,8,9,10,12,13,15,16 |
| 29 | 163.0756 | C10H11O2 | 5746 | 1 | 41 | 52 | 7,9,8,1,3,5,10,14,13,15,16,12 |
| | | | | | | 56.5 | 4,9,7,8,1,2,3,10,14,13,15,16,12,11 |
| 30 | 199.0962 | C10H15O4 | 652 | 3 | 45.5 | 52.5 | 5,3,1,6,7,9,4,0,2,11,12,16,15,13 |

FIG. 4

| atom index | unshifted | unshifted certain | unshifted | unshifted certain | unshifted specificity | Lost shifted | Lost certain | lost shifted specificity | Pre. Score | normalized |
|---|---|---|---|---|---|---|---|---|---|---|
| 0 | 2 | | | | | | | | | |
| 1 | 4 | 2 | | | | | | | | |
| 2 | 2 | 2 | | | | | | | | |
| 3 | 3 | 2 | | | | | | | | |
| 4 | 2 | 3 | | | | | | | | |
| 5 | 3 | 1 | | | | | | | | |
| 6 | 2 | 3 | | | | | | | | |
| 7 | 2 | 2 | 2 | 2 | 22.131578895 | 3 | 3 | 6.453088823 | 73.24416 | 0.72 |
| 8 | 2 | 2 | 2 | 2 | 22.131578895 | 3 | 3 | 6.453088823 | 73.24416 | 0.72 |
| 9 | 2 | 2 | 2 | 2 | 22.131578895 | 3 | 2.75 | 6.226622233 | 73.01769 | 0.72 |
| 10 | 3 | 3 | not considered, uncommon, or no shifted evidence | | | | | | | |
| 11 | 2 | 0 | | | | | | | | |
| 12 | 3 | 3 | 3 | 3 | 4.884370016 | 7 | 7 | 18.0294406 | 102.0877 | 1.00 |
| 13 | 3 | 3 | 3 | 3 | 4.884370016 | 7 | 7 | 18.0294406 | 102.0877 | 1.00 |
| 14 | 2 | 2 | 2 | 2 | 2.990430622 | 3 | 2.25 | 5.7289935 | 91.66211 | 0.90 |
| 15 | 3 | 3 | 3 | 3 | 4.884370016 | 7 | 7 | 18.0294406 | 102.0877 | 1.00 |
| 16 | 3 | 3 | 3 | 3 | 4.884370016 | 7 | 7 | 18.0294406 | 102.0877 | 1.00 |

FIG. 7

| atom index | unshifted certain | unshifted certain | unshifted specificity | Lost shifted | Lost certain | lost shifted specificity | pre-score | normalized score | type of oxidation (from DB) | common | additional reaction evidence | evidence found |
|---|---|---|---|---|---|---|---|---|---|---|---|---|
| 0 | | | | | | | | | | | | |
| 1 | | | | | | | | | | | | |
| 2 | | | | | | | | | | | | |
| 3 | | | | | | | | | | | | |
| 4 | | | | | | | | | | | | |
| 5 | | | | | | | | | | | | |
| 6 | not considered, uncommon, or no shifted evidence | | | | | | | | N-Hydroxylation of Primary Amines or Amides | no | | NA |
| 7 | 2 | 2 | 1 | 3 | 3 | 0.35791849 | 3.375827 | 0.70 | Aliphatic Hydroxylation | yes | H2O loss | no |
| 8 | 2 | 2 | 1 | 3 | 3 | 0.35791849 | 3.375827 | 0.70 | Aliphatic Hydroxylation | yes | H2O loss | no |
| 9 | 2 | 2 | 1 | 3 | 2.75 | 0.34535686 | 3.363267 | 0.70 | Aliphatic Hydroxylation | yes | H2O loss | no |
| 10 | | | | | | | | | | | | |
| 11 | not considered, uncommon, or no shifted evidence | | | | | | | | | | | |
| 12 | 3 | 3 | 0.220696962 | 7 | 7 | 1 | 4.797211 | 1 | Aromatic Hydroxylation | yes | none | NA |
| 13 | 3 | 3 | 0.220696962 | 7 | 7 | 1 | 4.797211 | 1 | Aromatic Hydroxylation | yes | none | NA |
| 14 | 3 | 2 | 0.135120628 | 3 | 2.25 | 0.31780761 | 4.200595 | 0.8756373 | Aromatic Hydroxylation | yes | none | NA |
| 15 | 3 | 3 | 0.220696962 | 7 | 7 | 1 | 4.797211 | 1 | Aromatic Hydroxylation | yes | none | NA |
| 16 | 3 | 3 | 0.220696962 | 7 | 7 | 1 | 4.797211 | 1 | Aromatic Hydroxylation | yes | none | NA |

FIG. 8

METHOD FOR PROPOSAL OF COMPOUND ANALOG STRUCTURES USING ACCURATE PRODUCT ION SPECTRA

CROSS REFERENCE TO RELATED APPLICATION

This application claims the benefit of U.S. Provisional Patent Application Ser. No. 62/440,963, filed Dec. 30, 2016, the content of which is incorporated by reference herein in its entirety.

INTRODUCTION

The teachings herein relate to determining a metabolic transformation applied to a known compound from tandem mass spectrometry spectra. More particularly the teachings herein relate to systems and methods that use the measured intensities of product ions of a known compound that has experienced a metabolic transformation to automatically score the atomic structural indices of the known compound for the likelihood of acquired or lost atoms from the metabolic transformation. The scores of the atomic structural indices are then used to determine the most likely structural transformation that was applied to the known compound during the metabolic transformation. The systems and methods herein can be performed in conjunction with a processor, controller, or computer system, such as the computer system of FIG. 1.

Metabolic Transformation Background

During a metabolic transformation, a metabolite (known compound) typically acquires one or more atoms or loses one or more atoms. A metabolic transformation of a metabolite is typically identified using tandem mass spectrometry (mass spectrometry/mass spectrometry (MS/MS)). Various methods of tandem mass spectrometry are described below. However, tandem mass spectrometry generally involves selecting a precursor ion or a range around the precursor ion, fragmenting the precursor ion or its range, and measuring the resulting product ion mass spectrum or mass-to-charge ratio (m/z) spectrum.

The tandem mass spectrometry can also be performed in conjunction with a separation device. In this case, a particular precursor ion may be selected and fragmented at a particular time in the separation, which is known as an elution time or retention time, for example.

A metabolic transformation of a known compound is identified by analyzing a sample that includes the known compound after the metabolic transformation has taken place. Using tandem mass spectrometry, the known compound (precursor ion) or a range around the known compound is selected and fragmented, producing a product ion mass spectrum.

If a separation device is used, the known compound may be selected at a retention time or a range of retention times. Note that the atoms acquired or lost during the metabolic transformation may cause the retention time of the metabolized known compound to vary from the retention time of the original known compound. As a result, the retention time of a precursor ion of a metabolized known compound relative to the retention time of the original known compound is used to infer the chemical nature of the known compound. Also note that if a range of retention times is used a plurality of product ion spectra may be produced for each metabolized known compound.

Accurate m/z values are obtained from the product ion spectrum for peaks in the spectrum. From these m/z values, molecular structures of the product ions fragmented from the metabolized known compound are determined. If a plurality of product ion spectra is available, a chromatographic peak may be obtained for each product ion. The retention times of chromatographic peaks may then also be used to correlate product ions to the metabolized known compound.

From the molecular structures of the product ions of the metabolized known compound, inferences are then made about the structure of the metabolized known compound. For example, if a certain product ion of the metabolized known compound is found to include a particular acquired atom or atoms it can suggest the location of the original known compound that acquired the atom or atoms.

Traditionally, inferences about metabolized known compounds from their product ions were made manually. In other words, a researcher would analyze the structures of the measured product ions of a metabolized known compound and compare these structures to the structure of the original or unmetabolized known compound. From this comparison, the researcher would make an inference about the structure of the metabolized known compound.

More recently, many software programs have been developed to automatically infer the structure of a metabolized known compound from its measured product ions. Exemplary software programs in this area include ACD/MS Fragmentor, Mass-MetaSite, and Mass Frontier/MetWorks. In general, these programs computationally fragment a known compound and compare the fragments to measured product ions.

Many of these automatic methods of inferring the structure of a metabolized known compound from its measured product ions fall short. As a result, additional systems and methods are needed. Such additional systems and methods are particularly needed to simplify and automate identification of proposed structures for metabolized compounds in a number of workflows. For example, these systems and methods are needed for metabolite identification in drug discovery (high throughput) or drug development (less common minor metabolites, including biologics). They are also needed for the identification of secondary endogenous metabolites (metabolomics) and compound derivatives (important for applied markets and forensics).

Tandem Mass Spectrometry Background

In general, tandem mass spectrometry, or MS/MS, is a well-known technique for analyzing compounds. Tandem mass spectrometry involves ionization of one or more compounds from a sample, selection of one or more precursor ions of the one or more compounds, fragmentation of the one or more precursor ions into fragment or product ions, and mass analysis of the product ions.

Tandem mass spectrometry can provide both qualitative and quantitative information. The product ions in the product ion spectrum can be used to identify a molecule of interest. The intensity of one or more product ions can be used to quantitate the amount of the compound present in a sample.

A large number of different types of experimental methods or workflows can be performed using a tandem mass spectrometer. Three broad categories of these workflows are, targeted acquisition, information dependent acquisition (IDA) or data-dependent acquisition (DDA), and data-independent acquisition (DIA).

In a targeted acquisition method, one or more transitions of a precursor ion to a product ion are predefined for a compound of interest. As a sample is being introduced into the tandem mass spectrometer, the one or more transitions are interrogated during each time period or cycle of a plurality of time periods or cycles. In other words, the mass spectrometer selects and fragments the precursor ion of each transition and performs a targeted mass analysis for the product ion of the transition. As a result, an intensity (a product ion intensity) is produced for each transition. Targeted acquisition methods include, but are not limited to, multiple reaction monitoring (MRM) and selected reaction monitoring (SRM).

In an IDA method, a user can specify criteria for performing an untargeted mass analysis of product ions, while a sample is being introduced into the tandem mass spectrometer. For example, in an IDA method a precursor ion or mass spectrometry (MS) survey scan is performed to generate a precursor ion peak list. The user can select criteria to filter the peak list for a subset of the precursor ions on the peak list. MS/MS is then performed on each precursor ion of the subset of precursor ions. A product ion spectrum is produced for each precursor ion. MS/MS is repeatedly performed on the precursor ions of the subset of precursor ions as the sample is being introduced into the tandem mass spectrometer.

In proteomics and many other sample types, however, the complexity and dynamic range of compounds are very large. This poses challenges for traditional targeted and IDA methods, requiring very high-speed MS/MS acquisition to deeply interrogate the sample in order to both identify and quantify a broad range of analytes.

As a result, DIA methods, the third broad category of tandem mass spectrometry, were developed. These DIA methods have been used to increase the reproducibility and comprehensiveness of data collection from complex samples. DIA methods can also be called non-specific fragmentation methods. In a traditional DIA method, the actions of the tandem mass spectrometer are not varied among MS/MS scans based on data acquired in a previous precursor or product ion scan. Instead, a precursor ion mass range is selected. A precursor ion mass selection window is then stepped across the precursor ion mass range. All precursor ions in the precursor ion mass selection window are fragmented and all of the product ions of all of the precursor ions in the precursor ion mass selection window are mass analyzed.

The precursor ion mass selection window used to scan the mass range can be very narrow so that the likelihood of multiple precursors within the window is small. This type of DIA method is called, for example, MS/MS$^{ALL}$. In an MS/MS$^{ALL}$ method, a precursor ion mass selection window of about 1 amu is scanned or stepped across an entire mass range. A product ion spectrum is produced for each 1 amu precursor mass window. The time it takes to analyze or scan the entire mass range once is referred to as one scan cycle. Scanning a narrow precursor ion mass selection window across a wide precursor ion mass range during each cycle, however, is not practical for some instruments and experiments.

As a result, a larger precursor ion mass selection window, or selection window with a greater width, is stepped across the entire precursor mass range. This type of DIA method is called, for example, sequential windowed (SWATH) acquisition. In a SWATH acquisition, the precursor ion mass selection window stepped across the precursor mass range in each cycle may have a width of 5-25 amu, or even larger. Like the MS/MS$^{ALL}$ method, all the precursor ions in each precursor ion mass selection window are fragmented, and all of the product ions of all of the precursor ions in each mass selection window are mass analyzed.

SUMMARY

A system, method, and computer program product are disclosed for identifying precursor ions originating from an ion source device using a scanning sequential windowed precursor ion selection and mass analysis survey scan. All three embodiments include the following steps.

An ion source device ionizes a first sample. The ion source device produces an ion beam.

The first sample includes a known compound that has experienced a metabolic chemical transformation. One or more chemical transformation may occur.

A tandem mass spectrometer selects a precursor ion of the metabolized known compound from the ion beam. It then fragments the precursor ion. At least one metabolized product ion spectrum for the metabolized known compound is produced.

A processor receives the at least one metabolized product ion spectrum from the tandem mass spectrometer. It infers a plurality of metabolized product ion chemical structures from m/z peaks of the at least one metabolized product ion spectrum.

The processor receives at least one unmetabolized product ion spectrum obtained by ionizing a second sample. The second sample includes an unmetabolized version of the known compound. The at least one unmetabolized product ion spectrum is obtained by selecting and fragmenting a precursor ion of the unmetabolized version of the known compound. The processor infers a plurality of unmetabolized product ion chemical structures from m/z peaks of the at least one unmetabolized product ion spectrum.

The first sample and the second sample may be analyzed in any order. Also, in some embodiments, the metabolized product ion spectrum and the unmetabolized product ion spectrum may be obtained from the same sample.

The processor compares each metabolized chemical structure of the plurality of metabolized product ion chemical structures to each unmetabolized chemical structure of the plurality of unmetabolized product ion chemical structures. One or more matched metabolized product ion chemical structures and one or more unmatched metabolized product ion chemical structures are produced.

For each unmatched structure of the one or more unmatched metabolized product ion chemical structures, the processor performs two steps. First, it searches a biotransformation repository for one or more chemical modifications to each unmatched structure. Second, it compares each unmatched structure and the one or more chemical modifications found to the plurality of unmetabolized product ion chemical structures. This produces one or more modified matched metabolized product ion chemical structures.

For each atomic index of the chemical structure of the unmetabolized known compound, the processor performs three steps. First, it calculates an unmodified intensity specificity from the one or more matched metabolized product ion chemical structures that include each atomic index. Second, it calculates a modified intensity specificity from the one or more modified matched metabolized product ion chemical structures that include each atomic index. Finally, it calculates a score from the unmodified intensity specificities of the other atomic indices and the modified intensity specificity of the atomic index.

The processor identifies one or more atomic indices of the chemical structure of the unmetabolized known compound with the highest score as one or more sites of modification of the metabolized known compound found in the first sample.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

FIG. 4 is an exemplary table that shows how the 30 product ions found for unmetabolized methocarbamol are mapped to the structural indices, in accordance with various embodiments.

FIG. 7 is an exemplary table that shows how the 17 structural indices of unmetabolized methocarbamol are scored for their likelihood of including the modification of the metabolized methocarbamol based on the product ions of the metabolized methocarbamol, in accordance with various embodiments.

FIG. 8 is an exemplary table that shows how the specificities of the 17 structural indices of unmetabolized methocarbamol calculated in FIG. 7 are normalized before calculating their scores, in accordance with various embodiments.

Figure 1:
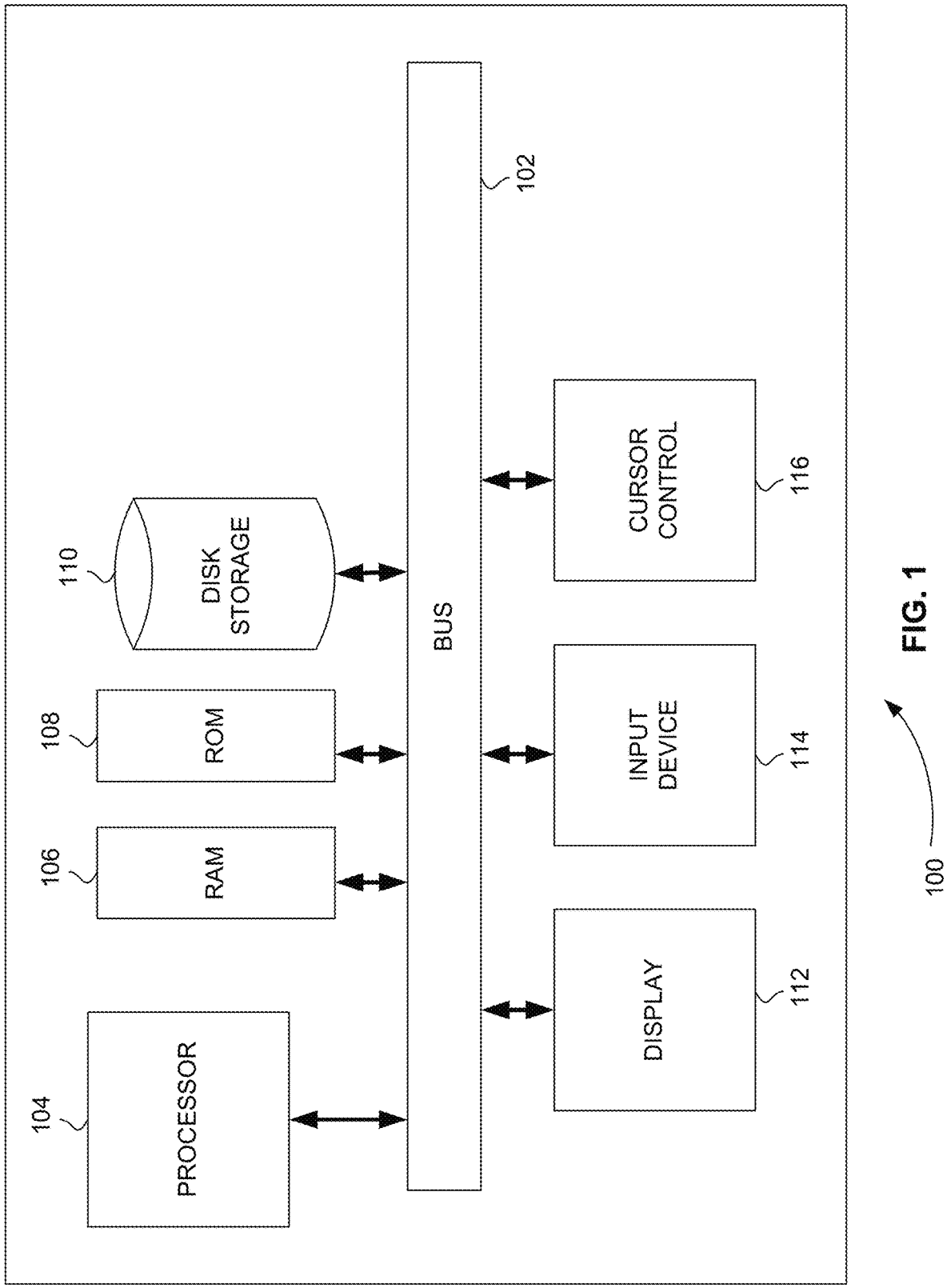
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Identifying the Structure of a Metabolite

Embodiments of systems and methods for identifying the structure of a metabolite are described in this detailed description of the invention. In this detailed description, for purposes of explanation, numerous specific details are set forth to provide a thorough understanding of embodiments of the present invention. One skilled in the art will appreciate, however, that embodiments of the present invention may be practiced without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of embodiments of the present invention.

As described above, inferences about metabolized known compounds from their product ions were traditionally made manually. In other words, a researcher would analyze the structures of the measured product ions of a metabolized known compound and compare these structures to the structure of the original or unmetabolized known compound. More recently, many software programs have been developed to automatically infer the structure of a metabolized known compound from its measured product ions. However, these automatic methods of inferring the structure of a metabolized known compound from its measured product ions often fall short. As a result, additional systems and methods are needed.

In various embodiments, systems and methods are provided that automatically propose and rank structures for a metabolized known compound based on (1) chemical knowledge from a biotransformation repository or database, (2) the known structure of the unmetabolized known compound and the measured product ion spectrum for the unmetabolized known compound, and (3) a measured product ion spectrum for the metabolized known compound.

A biotransformation repository can be, but is not limited to, a database, a data set, or a computer file. The biotransformation repository includes a plurality of possible chemical reactions that are known to take place in biotransformations that occur in one or more metabolic processes. Information about the chemical reactions that is stored in the biotransformation repository includes, for example, candidate chemical substructures where the reaction takes place, whether the reaction is common, the reaction itself (a mapping of the atoms before and after), and a biotransformation (reaction) signature. The biotransformation signature, for example, can include the mass or m/z shift of the reaction, common product ions involved in the reaction, and/or neutral losses that are characteristic for the reaction, including their abundance.

The biotransformation repository is used to determine potential sites of modification on the known structure of the unmetabolized known compound. These potential sites of modification can also be called atomic structural indices.

The potential sites of modification are found on the unmetabolized known compound by performing a tandem mass spectrometry analysis of the unmetabolized known compound. From the product ion mass spectrum obtained from the analysis, the exact mass or m/z value of each product ion of the unmetabolized known compound is obtained. From the exact mass, the structures of the product ions are inferred. These structures of the product ions are associated with the structural indices of the unmetabolized known compound. This association is done, for example, using annotated product ion scoring. Annotated product ion scoring is described in U.S. patent application Ser. No. 15/310,845 (hereinafter the "'845 Application"), which is incorporated by reference herein in its entirety. Essentially annotated product ion scoring keeps track of the atoms (excluding hydrogen atoms) that constitute each product ion of the unmetabolized known compound.

The analysis of the unmetabolized known compound using tandem mass spectrometry can be performed once and the results can be stored in a database, data set, or computer file, for example. The same results can then be used each time a sample is analyzed that includes a metabolized version of the known compound.

When a sample containing a metabolized version of the known compound is analyzed using tandem mass spectrometry, a product ion spectrum is produced for the metabolized known compound. From the product ion mass spectrum, the exact mass or m/z value of each product ion of the metabolized known compound is obtained. From the exact mass, the structures of the product ions are inferred.

The structures of the product ions of the metabolized known compound are then compared to the structures of the product ions of the original or unmetabolized known compound. The structures of the two sets of product ions are compared for both commonality and differences using the biotransformation repository. In other words, each structure of each product ion of the metabolized known compound and each structure of each product ion of the unmetabolized known compound are compared taking into account all possible applicable biotransformation signatures obtained from the biotransformation repository.

In various embodiments, each structure of each product ion of the metabolized known compound and each structure of each product ion of the unmetabolized known compound are compared by also taking into account all possible applicable biotransformation signatures obtained from the compound itself by breaking labile bonds, such as carbon-nitrogen (C—N) bond. In other words, in addition to the biotransformation database, rules regarding the breaking of labile bonds are used.

More specifically, product ions of the metabolized and unmetabolized compounds are compared by taking into account mass shifts and neutral losses known to occur in biotransformations. Biotransformations that result in a loss of part of an unmetabolized compound structure are located on the molecule first, removed, and the remaining portion of the molecule serves as a "unmetabolized compound substitute" for a further structural proposal.

For example, for a single biotransformation (oxidation having a shift of +16 with a potential resulting loss of water +16−18=−2) the atom can be a part of an unchanged product ion or a shifted product ion. For a demethylation (cleavage) loss, multiple atoms involved may be grouped into one superatom that is either unchanged or lost. All possible atom states (unchanged, reaction 1, reaction 2, reaction 1 and 2) are tracked for combinations of reactions. In case of multiple matches (both shifted and unshifted product ions that align), the best match is determined based on relative intensities of product ions in the product ion mass spectra of unmetabolized and metabolized compounds.

Each structural index of the unmetabolized known compound is scored based on how it is explained by the product ions of the unmetabolized known compound. The score includes product ion specificity (how big—how many atoms and how unique the product ion is) and fragment intensity. Once all scores for all possible structural indices are obtained, they are normalized for each possible state. Then a total score is determined for each index or site of modification, summing the scores for applicable changed and unchanged atom states. Potential sites of modifications are ranked according to the total scores and scores can be used to cut off the less probable sites of modifications.

Example Data

Systems and methods that automatically propose and rank structures for a metabolized known compound in accordance with various embodiments are described here by way of an example. In this example, methocarbamol is the unmetabolized known compound. A sample is obtained in which methocarbamol has experienced a metabolic transformation. The metabolic transformation in this example is the oxidation of methocarbamol. The goal in this example is to determine the structure of the oxidized methocarbamol, which is the metabolized known compound. In other words, the goal is to determine what part of methocarbamol received an oxygen atom during the metabolic transformation.

Systems and methods in accordance with various embodiments begin this determination by indexing the atomic structure of the unmetabolized known compound methocarbamol.

Figure 2:
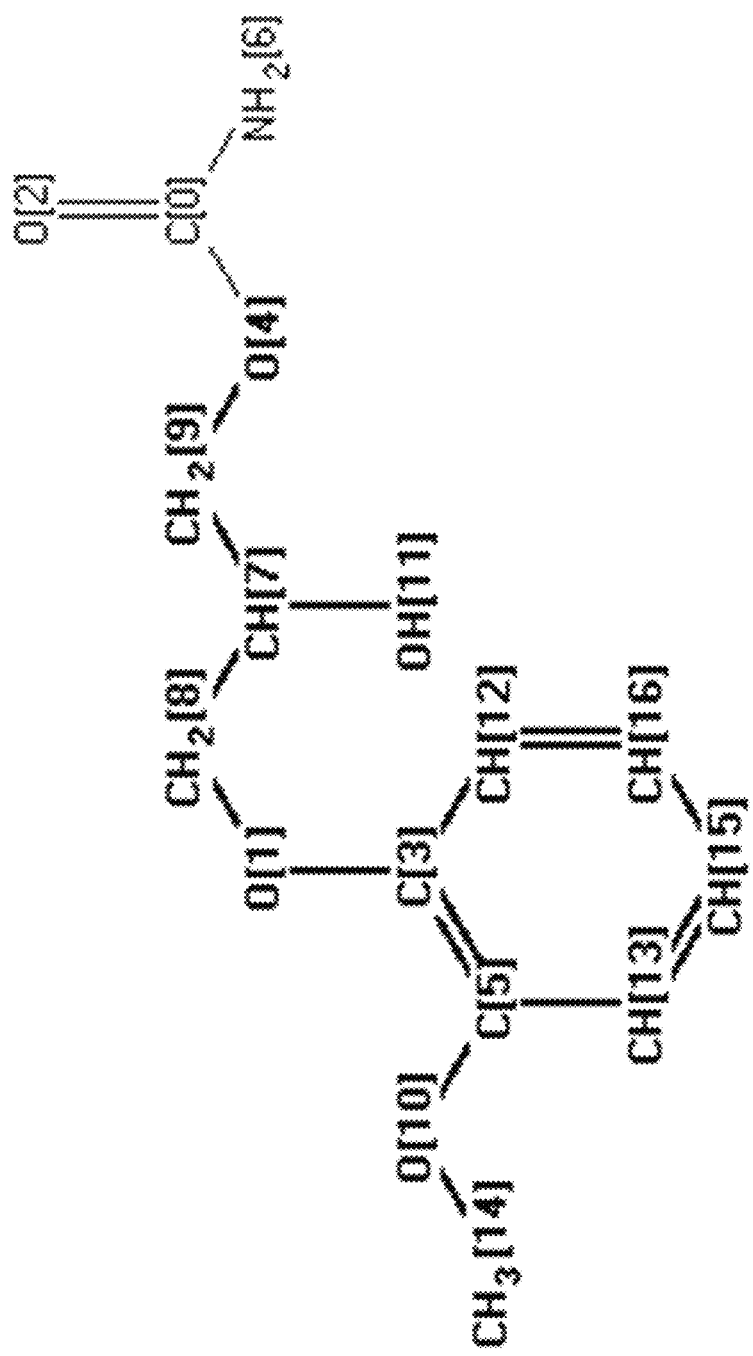
FIG. 2 is a diagram of the unmetabolized known compound methocarbamol that includes atomic structural indices, in accordance with various embodiments.

FIG. 2 is a diagram 200 of the unmetabolized known compound methocarbamol that includes atomic structural indices, in accordance with various embodiments. As shown in the figure, unmetabolized methocarbamol includes 17 indices (0-16) that identify the structural locations of the atoms of methocarbamol other than hydrogen.

A sample that only includes unmetabolized methocarbamol is then analyzed using tandem mass spectrometry to find the product ions of unmetabolized methocarbamol. From this analysis, one or more product ion mass spectra are obtained for the unmetabolized methocarbamol. A plurality of product ion mass spectra can be obtained by separating the methocarbamol over time and analyzing the separation over a range of times using the mass spectrometer, for example. Methocarbamol is known to have a retention time of 8.57 min., so product ions in one or more ion spectra at or near a retention time of 8.57 min. can be identified as product ions of methocarbamol, for example.

Figure 3:
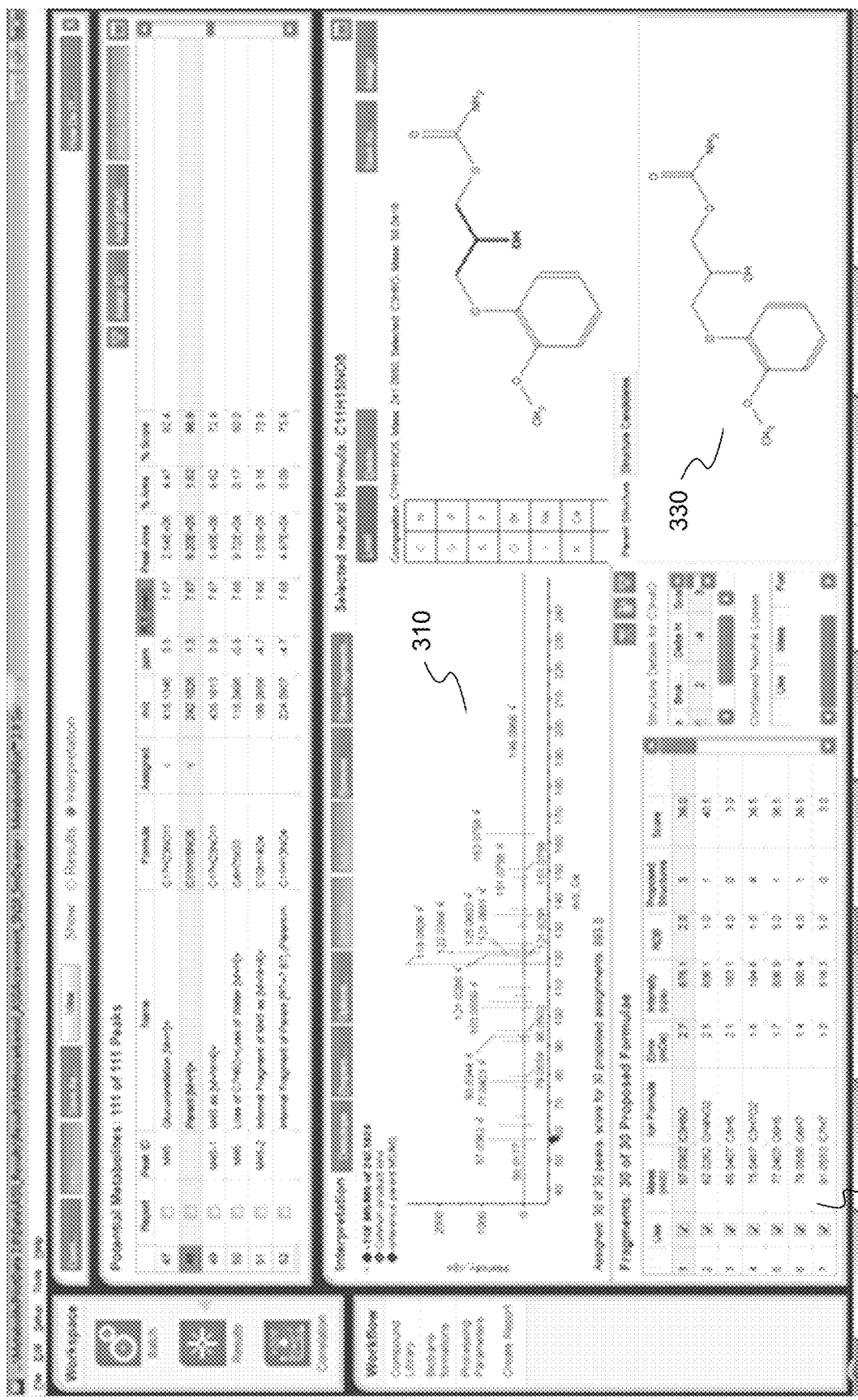
FIG. 3 is an exemplary screen capture from Sciex's METABOLITEPILOT™ metabolite identification software showing the results from analyzing the unmetabolized known compound methocarbamol using tandem mass spectrometry, in accordance with various embodiments.

FIG. 3 is an exemplary screen capture 300 from Sciex's METABOLITEPILOT™ metabolite identification software showing the results from analyzing the unmetabolized known compound methocarbamol using tandem mass spectrometry, in accordance with various embodiments. Screen capture 300 shows the product ion mass spectrum 310 obtained for the unmetabolized methocarbamol. It also shows a table 320 listing the product ions inferred from product ion mass spectrum 310, and a diagram 330 of the chemical structure of the unmetabolized methocarbamol, also called the parent structure.

After obtaining the product ions of unmetabolized methocarbamol, they are mapped to the structural indices of methocarbamol. This mapping is done, for example, using the annotated product ion scoring of the '845 Application, as described above.

FIG. 4 is an exemplary table 400 that shows how the 30 product ions found for unmetabolized methocarbamol are mapped to the structural indices, in accordance with various embodiments. For example, the first product ion 410 is found to have an accurate mass of 57.0367 m/z. From this accurate mass, the ion formula $C_3H_5O$ is inferred with an annotated product ion score of 36. This ion formula or chemical structure is then mapped to the structural indices of methocarbamol.

Table 400 shows that first product ion 410, $C_3H_5O$, can be mapped to the structural indices of methocarbamol in three different ways: 7, 8, 9, and 11; 4, 7, 8, and 9; and 1, 7, 8, and 9. Note that the indices 7, 8, and 9 are considered to be certain, because all three solutions include them. The indices 1, 4, and 11 are considered to be uncertain, because all of the solutions do not include them. Also note that each solution is scored. The scores take into account the number of bonds broken to create product ion 410, for example.

Further note that the information shown in FIGS. 2-4 is obtained from analyzing a sample containing only unmetabolized methocarbamol. This information may be obtained each time a sample containing metabolized methocarbamol is analyzed by performing a separate tandem mass spectrometry experiment. Alternatively, a sample containing only unmetabolized methocarbamol may be analyzed once and the information shown in FIGS. 2-4 may be stored and reused multiple times.

A sample containing metabolized methocarbamol is analyzed using tandem mass spectrometry in a similar fashion to a sample containing only unmetabolized methocarbamol. One or more product ion mass spectra are obtained for the metabolized methocarbamol and the chemical structures of product ions are inferred from the one or more product ion mass spectra.

A difference in the two analyses occurs however in how product ions for the metabolized methocarbamol are compared to the structural indices of the unmetabolized methocarbamol. This comparison must take into account the fact that the product ions may be modified. This is done by accessing the biotransformation repository. For example, product ions found for the metabolized methocarbamol that are not common to the unmetabolized methocarbamol can be searched against the biotransformation repository. If a biotransformation is found in the repository that explains a difference between the product ion of the metabolized methocarbamol and a product ion of the unmetabolized methocarbamol, then the product ion of the metabolized methocarbamol can be used to identify the structure of the metabolized methocarbamol.

Figure 5:
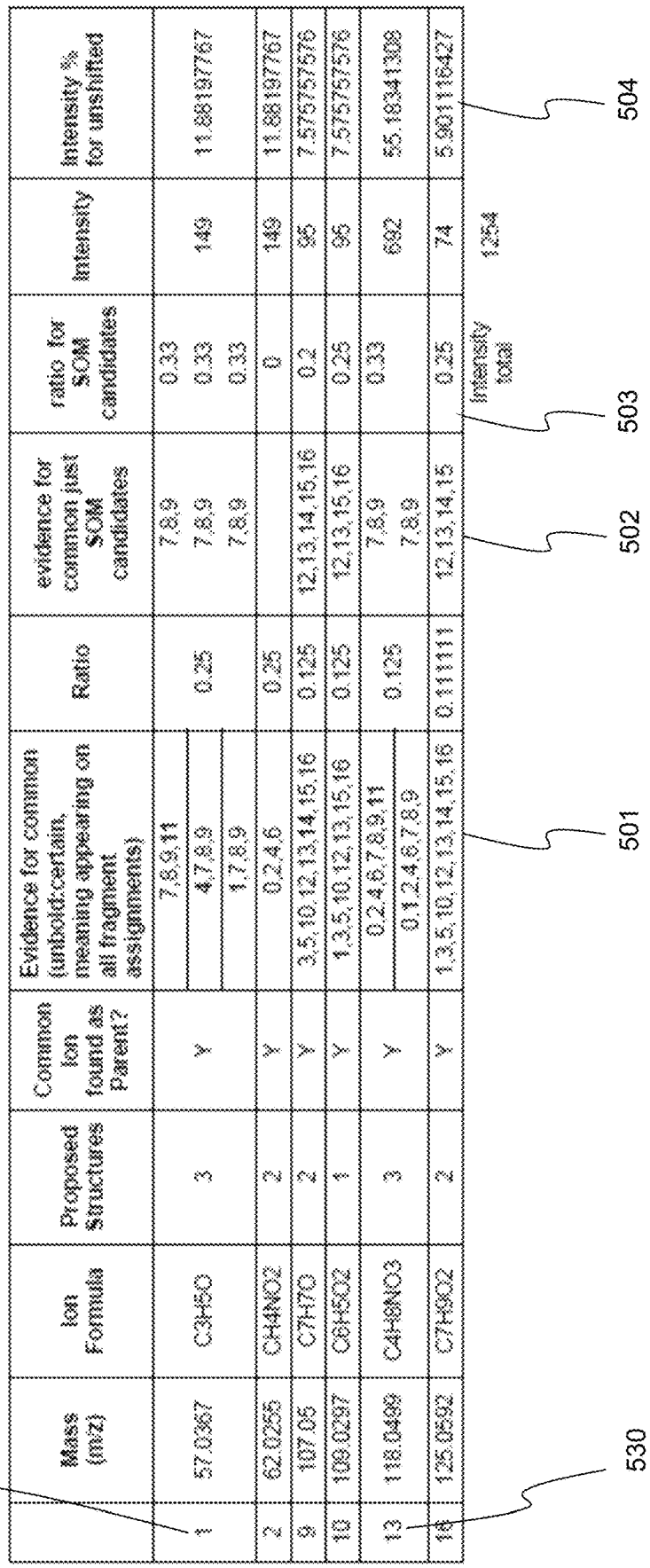
FIG. 5 is an exemplary table that shows six product ions found for metabolized methocarbamol that are found to match product ions of the unmetabolized methocarbamol without any shifts in mass, in accordance with various embodiments.

FIG. 5 is an exemplary table 500 that shows six product ions found for metabolized methocarbamol that are found to match product ions of the unmetabolized methocarbamol without any shifts in mass, in accordance with various embodiments. The product ions of table 500 are mapped to the structural indices of unmetabolized methocarbamol. For example, the first product ion 510 is found to have an accurate mass of 57.0367 m/z. From this accurate mass, the ion formula $C_3H_5O$ is inferred. This ion formula or chemical structure is then mapped to the structural indices of methocarbamol just like first product ion 410 of FIG. 4. In other words, product ion 510 of FIG. 5 and first product ion 410 of FIG. 4 are common product ions.

Figure 6:
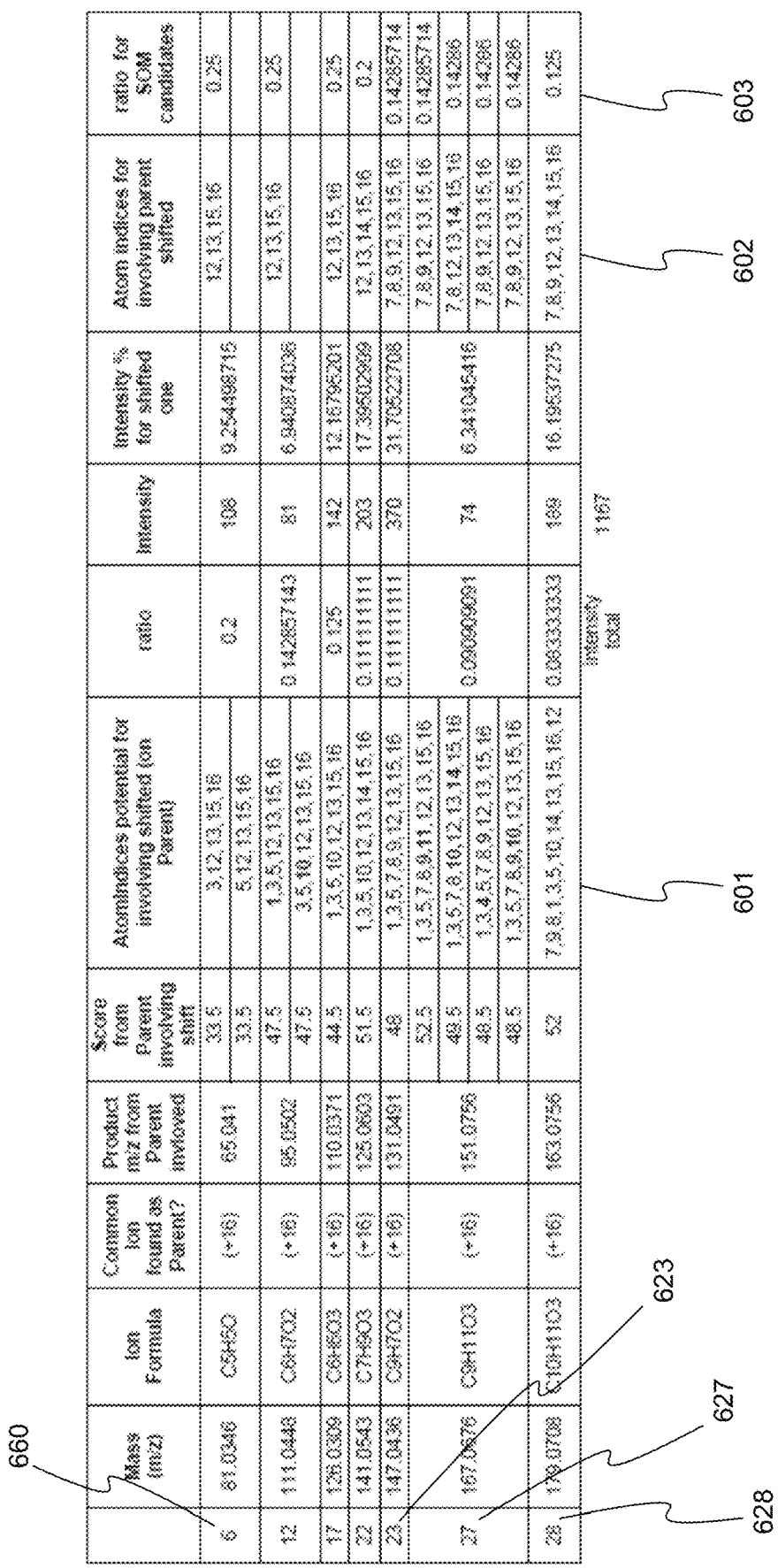
FIG. 6 is an exemplary table that shows seven product ions found for metabolized methocarbamol that are found to match product ions of the unmetabolized methocarbamol with a shift in mass of +16, in accordance with various embodiments.

FIG. 6 is an exemplary table 600 that shows seven product ions found for metabolized methocarbamol that are found to match product ions of the unmetabolized methocarbamol with a shift in mass of +16, in accordance with various embodiments. The product ions of table 600 are mapped to the structural indices of unmetabolized methocarbamol with the help of a biotransformation repository. For example, sixth product ion 660 is found to have an accurate mass of 81.0346 m/z. From this accurate mass, the ion formula $C_5H_5O$ is inferred. When mapped to the structure of the unmetabolized methocarbamol, this product ion does not appear to have a product ion in common with the unmetabolized methocarbamol.

At this point, however, product ion 660 is searched against the biotransformation repository. As a result of the search, it is determined that this product ion can be a modified form of a product ion of the unmetabolized methocarbamol. In particular, product ion 660, $C_5H_5O$, of the metabolized methocarbamol is an oxidized form of product ion 430 in FIG. 4, $C_5H_5$, of the unmetabolized methocarbamol. In other words, from the biotransformation repository it is learned that product ion 660 of FIG. 6 is shifted by +16 (an oxygen atom) due to a metabolic transformation. Consequently, product ion 660 is found to be a shifted product ion of the metabolized methocarbamol.

As FIGS. 5 and 6 show, the product ions of the metabolized methocarbamol includes both unshifted and shifted product ions. The unshifted and shifted product ions are scored based on their intensities in the one or more product ion mass spectra. The scores of the unshifted and shifted product ions are then used to score the structural indices of the unmetabolized methocarbamol. The scores of the structural indices of the unmetabolized methocarbamol, in turn, are used to determine the most likely location of the modification on the metabolized methocarbamol. In other words, the scores of the structural indices of the unmetabolized methocarbamol are used to determine the most likely location of the additional oxygen atom on the metabolized or oxidized methocarbamol.

FIG. 7 is an exemplary table 700 that shows how the 17 structural indices of unmetabolized methocarbamol are scored for their likelihood of including the modification of the metabolized methocarbamol based on the product ions of the metabolized methocarbamol, in accordance with various embodiments. Essentially, the purpose of table 700 is to determine the most likely location or structural index for the metabolic modification on methocarbamol. In order to do this, a score or pre-score is calculated for the structural indices in table 700. The pre-score, therefore, indicates the likelihood that the index is the location of the metabolic modification, which is oxidation in this example.

In this example, only the structural indices that correspond to product ions that are found to match shifted product ions of the unmetabolized methocarbamol are scored. In other words, only the indices that correspond to the product ions shown in FIG. 6 are scored.

In addition, not all the indices that potentially match the product ions in FIG. 6 are scored. For example, there may be no site of modification (SOM) evidence in the biotransformation repository that a particular index can include the modification even though that index can theoretically include the modification. FIG. 6 includes for each product ion both the potential indices and the evidence supported indices. The potential indices are shown in column 601. The evidence supported indices are shown in column 602. As a result, in this example only the indices shown in column 602 are scored.

Therefore, in FIG. 7 only indices 7, 8, 9, 12, 13, 14, 15, and 16 are scored. In other words, indices 0, 1, 2, 3, 4, 5, 6, 10, and 11 are not scored. In various alternative embodiments, all indices can be scored. However, reducing the number of indices that are scored increases competition efficiency.

In FIG. 7, an unshifted and shifted specificity is calculated for each scored index. The unshifted specificity is the specificity if the index does not include the modification. The shifted specificity is the specificity if the index does include the modification.

The unshifted specificity is calculated from the product ions that are found to match product ions of the unmetabolized methocarbamol without a shift. In other words, the unshifted specificity is calculated using the product ions of FIG. 5. Like FIG. 6, FIG. 5 also includes both potential indices and evidence supported indices. The potential indices are shown in column 501 of FIG. 5. The evidence supported indices are shown in column 502. In this example, the unshifted specificity is calculated based on values related to the evidence supported indices shown in column 502.

For example, index 9 appears in column 502 of FIG. 5 for first product ion 510 and 13th product ion 530. As a result, the unshifted specificity of index 9 is calculated from intensities of first product ion 510 and 13th product ion 530.

The specificity of a particular product ion is calculated as a percentage. It is the percentage of the total intensities measured that the intensity of that particular product ion represents. The equation for the specificity of particular product ion is shown below as Equation 1.

$$Specificity_{production} = \frac{Intensity_{production}}{\sum Intensity_{production}} \times 100 \quad (1)$$

In FIG. 5, the specificity of a particular product ion is shown in column 504 and is referred to as the intensity percentage for unshifted product ions. The specificities for first product ion 510 and 13th product ion 530 shown in FIG. 5 are 11.88197767 and 55.18341308, respectively.

The specificity of a particular evidence supported index is the sum of the specificities of each of its product ions is multiplied by its ratio or percentage of that index to the other indices of the product ion. The equation for the specificity of a particular evidence supported index is shown below as Equation 2.

$$Specificity_{index} = \Sigma Ratio_{index} \times Specificity_{product\ ion} \quad (2)$$

As described above, index 9 appears in column 502 of FIG. 5 for first product ion 510 and 13th product ion 530. The ratio of index 9 to the total number indices in first product ion 510 is shown in column 503 and is 0.33. The ratio multiplied by the specificity of first product ion 510 is then 0.33×11.88197767. Similarly, the ratio of index 9 to the total number of indices of 13th product ion 530 is shown in column 503 and is 0.33. This ratio multiplied by the specificity of 13th product ion 510 is then 0.33×55.18341308. The total specificity for the unshifted index 9 is then 0.33×11.88197767+0.33×55.18341308, or 22.13157895.

This unshifted specificity value is shown in column 701 and row 710 of FIG. 7 for index 9. The shifted specificity of index 9, shown in column 703 and row 710, is similarly calculated from the shifted product ions of FIG. 6 using Equations 1 and 2.

In FIG. 6, index 9 appears in column 602 for 23rd product ion 623, 27th product ion 627 and 28th product ion 628. The ratio of index 9 to the total number of indices of 23rd product ion 623 is shown in column 603 and is 0.14285714. The ratio multiplied by the specificity of 23rd product ion 623 is then 0.14285714×31.70522708. Similarly, ratio of index 9 to the total number of indices of 28th product ion 628 is shown in column 603 and is 0.125. This ratio multiplied by the specificity of 28th product ion 628 is then 0.125×16.19537275.

Finally, the ratio of index 9 to the total number of indices of 27th product ion 627 is shown in column 603 and is 0.14286. The ratio multiplied by the specificity of 27th product ion 623 is then 0.14286×6.341045426. Note, however, that index 9 is not certain in the solutions for 27th product ion 627 shown in column 602. In other words, index 9 appears in only three of the four solutions. This uncertainty is taken into account in the calculation. In other words, instead of using 0.14286×6.341045426, this value is further multiplied by the certainty. The certainty is the ratio of the solutions containing the index (three) to the total number of solutions (four) solutions or 0.75. So the calculation for the 27th product ion 623 is then 0.75×0.14286×6.341045426. The equation for the specificity of a particular evidence supported index if the certainty of the index is taken into account is shown below as Equation 3.

$$Specificity_{index} = \Sigma Certainty_{index} \times Ratio_{index} \times Specificity_{product\ ion} \quad (3)$$

The total specificity for the shifted index 9 is then 0.14285714×31.70522708+0.125×16.19537275+0.75× 0.14286×6.341045426, or 6.22662233. This unshifted specificity value is shown in column 703 and row 710 of FIG. 7 for index 9.

A score is calculated for each evidence supported index. Scores calculated for each of the evidence supported indices of the example are shown in FIG. 7.

In various embodiments, before calculation, indices can be merged into groups (molecule regions) based on the same scores for "shifted" and "unshifted" evidence. For example, in FIG. 7 indices 7 and 8 may be merged into a group or group index, and indices 12, 13, 15 and 16 may be merged into another group or group index.

The score of each index or group is listed in column 704 and is called pre-score in FIG. 7. The score for each index is the sum of the shifted specificity of that index and unshifted specificities of the other evidence supported indices. The equation for the score of an index is shown below as Equation 4.

$$Score_{index} = Shifted\ Specificity_{index} + \sum Unshifted\ Specificity_{each\ other\ index} \quad (4)$$

For example, the score for index 9 shown in column 704 and row 710 of FIG. 7 is 73.01769. This value is calculated by summing the shifted specificity of index 9 and the unshifted specificities of indices 7, 8, 12, 13, 14, 15, and 16.

In column 705, the scores of column 704 are normalized to the highest score, which is 102.0677. In other words, each score of column 704 is divided by 102.0677.

This normalization essentially ranks the evidence supported indices. As a result, it can be seen from column 705 that indices 12, 13, 15, and 16 are the indices most likely to be the site of modification. In other words, the metabolized methocarbamol is most likely to include oxygen at one of these indices.

In various embodiments, the specificities of the indices can be normalized for calculating the score. This is shown in the next figure.

FIG. 8 is an exemplary table 800 that shows how the specificities of the 17 structural indices of unmetabolized methocarbamol calculated in FIG. 7 are normalized before calculating their scores, in accordance with various embodiments. The values shown in column 801 of FIG. 8 are the unshifted specificities of the column 701 of FIG. 7 divided by the largest specificity, 22.13157895. The values shown in column 803 of FIG. 8 are the shifted specificities of column 703 of FIG. 7 divided by the largest specificity, 18.0294406.

As in FIG. 7, the score or pre-score shown in column 804 of FIG. 8 is calculated according to Equation 4. In column 805, the scores of column 804 are normalized to the highest score, which is 4.797211. In other words, each score of column 804 is divided by 4.797211.

Again, as in FIG. 7, the normalization in FIG. 8 essentially ranks the evidence supported indices. As a result, it can be seen from column 805 that indices 12, 13, 15, and 16 are the indices most likely to be the site of modification. In other words, the metabolized methocarbamol is most likely to include oxygen at one of these indices.

System for Identifying Site of Modification

Figure 9:
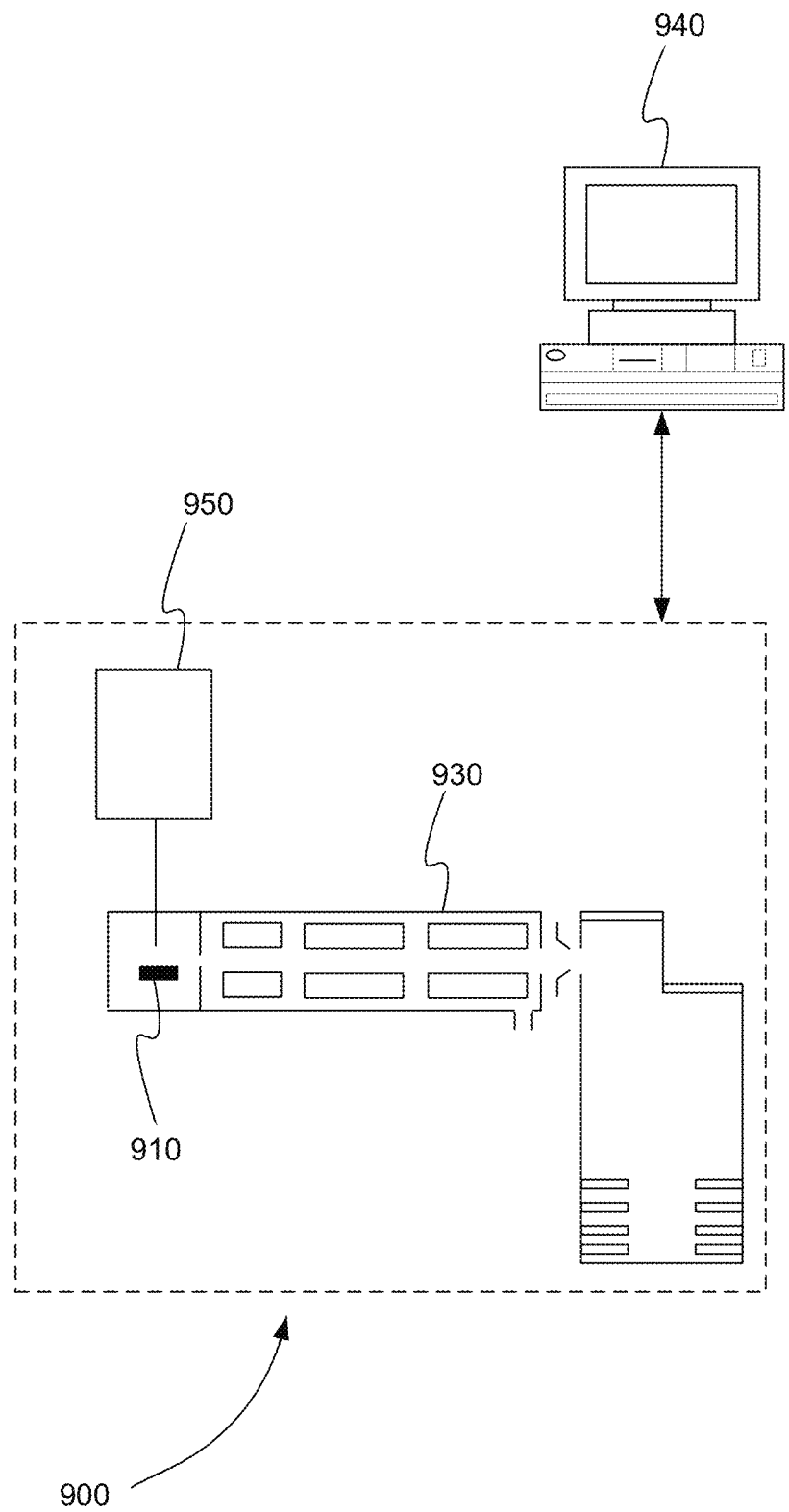
FIG. 9 is a schematic diagram of a system for identifying the site of modification of a metabolized known compound using tandem mass spectrometry, in accordance with various embodiments.

FIG. 9 is a schematic diagram of a system 900 for identifying the site of modification of a metabolized known compound using tandem mass spectrometry, in accordance with various embodiments. System 900 includes ion source device 910, tandem mass spectrometer 930, and processor 940. System 900 further optionally includes sample introduction device 950.

Ion source device 910 ionizes a first sample. The first sample includes a known compound that has experienced a metabolic chemical transformation. Ion source device 910 produces an ion beam. Ion source device 910 can perform ionization techniques that include, but are not limited to, matrix assisted laser desorption/ionization (MALDI) or electrospray ionization (ESI).

Tandem mass spectrometer 930 selects a precursor ion of the metabolized known compound from the ion beam. It then fragments the precursor ion. At least one metabolized product ion spectrum for the metabolized known compound is produced. Tandem mass spectrometer 930 can include one or more mass spectrometry stages, cells, or device for selecting and fragmenting precursor ions and for detecting product ions. One of ordinary skill in the art can appreciate that a stage of tandem mass spectrometer 930 can be, but is not limited to, a quadrupole, an ion trap, an orbitrap, an ion mobility device, a Fourier transform ion cyclotron resonance (FT-ICR) device, or a time-of-flight (TOF) device.

Processor 940 can be, but is not limited to, a computer, a microprocessor, the computer system of FIG. 1, or any device capable of sending and receiving control signals and data from tandem mass spectrometer 930 and processing data. Processor 940 is in communication with tandem mass spectrometer 930.

Processor 940 receives the at least one metabolized product ion spectrum from tandem mass spectrometer 930. It infers a plurality of metabolized product ion chemical structures from mass-to-charge ratio (m/z) peaks of the at least one metabolized product ion spectrum.

Processor 940 receives at least one unmetabolized product ion spectrum. The at least one unmetabolized product ion spectrum may be obtained from the first sample or may be obtained by ionizing a second sample. The second sample includes, for example, an unmetabolized version of the known compound. The at least one unmetabolized product ion spectrum is obtained by selecting and fragmenting a precursor ion of the unmetabolized version of the known compound. Processor 940 infers a plurality of unmetabolized product ion chemical structures from m/z peaks of the at least one unmetabolized product ion spectrum.

Processor 940 compares each metabolized chemical structure of the plurality of metabolized product ion chemical structures to each unmetabolized chemical structure of the plurality of unmetabolized product ion chemical structures. One or more matched metabolized product ion chemical structures and one or more unmatched metabolized product ion chemical structures are produced. The one or more matched metabolized product ion chemical structures are, for example, the unshifted product ions of FIG. 5.

For each unmatched structure of the one or more unmatched metabolized product ion chemical structures, processor 940 performs two steps. First, it searches a biotransformation repository for one or more chemical modifications to each unmatched structure. Second, it compares each unmatched structure and the one or more chemical modifications found to the plurality of unmetabolized product ion chemical structures. This produces one or more modified matched metabolized product ion chemical structures. The one or more modified matched metabolized product ion chemical structures are, for example, the shifted product ions of FIG. 6.

For each atomic index of the chemical structure of the unmetabolized known compound, processor 940 performs three steps. First, it calculates an unmodified intensity specificity from the one or more matched metabolized product ion chemical structures that include each atomic index. Second, it calculates a modified intensity specificity from the one or more modified matched metabolized product ion chemical structures that include each atomic index. Finally, it calculates a score from the unmodified intensity specificities of the other atomic indices and the modified intensity specificity of the atomic index.

Processor 940 identifies one or more atomic indices of the chemical structure of the unmetabolized known compound with the highest score as one or more sites of modification of the metabolized known compound found in the first sample.

In various embodiments, each atomic index of the chemical structure of the unmetabolized known compound is an atomic index of an element other than hydrogen.

In various embodiments, processor 940 receives the at least one unmetabolized product ion spectrum from a database, data set, or computer file where the at least one unmetabolized product ion spectrum is stored.

In various embodiments, processor 940 receives the at least one unmetabolized product ion spectrum from tandem mass spectrometer 930 after analyzing a second sample. Before or after analyzing the first sample, ion source device 910 ionizes the second sample. An ion beam is produced and tandem mass spectrometer 930 selects an unmetabolized precursor ion of the unmetabolized known compound from the ion beam and fragments the unmetabolized precursor ion. The at least one unmetabolized product ion spectrum is produced for the unmetabolized known compound.

In various alternative embodiments, processor 940 receives the at least one unmetabolized product ion spectrum from tandem mass spectrometer 930 after analyzing the same first sample. Before or after analyzing the metabolized known compound, tandem mass spectrometer 930 selects an unmetabolized precursor ion of the unmetabolized known compound from the ion beam of the first sample and fragments the unmetabolized precursor ion, producing at least one unmetabolized product ion spectrum for the unmetabolized known compound.

In various embodiments, the one or more chemical modifications includes a shift in m/z or a neutral loss.

In various embodiments, for each atomic index of the chemical structure of the unmetabolized known compound, processor 940 calculates an unmodified intensity specificity from the one or more matched metabolized product ion chemical structures according to $$\text{Specificity}_{index} = \Sigma \text{Ratio}_{index} \times \text{Specificity}_{product\ ion}.$$

$\text{Ratio}_{index}$ is the ratio of the index to total number of indices in each product ion structure of the one or more matched metabolized product ion chemical structures. $\text{Specificity}_{product\ ion}$ is the intensity specificity of each product ion structure of the one or more matched metabolized product ion chemical structures. This is calculated according to $$\text{Specificity}_{production} = \frac{\text{Intensity}_{production}}{\sum \text{Intensity}_{production}} \times 100.$$

$\text{Intensity}_{product\ ion}$ is the intensity measured by tandem mass spectrometer 930 for each product ion structure of the one or more matched metabolized product ion chemical structures. $\Sigma \text{Intensity}_{product\ ion}$ is the sum of the intensities measured for all of the one or more matched metabolized product ion chemical structures.

In various embodiments, for each atomic index of the chemical structure of the unmetabolized known compound, processor 940 calculates an unmodified intensity specificity from the one or more matched metabolized product ion chemical structures according to $$Specificity_{index} = \Sigma Certainty_{index} \times Ratio_{index} \times Specificity_{product\ ion}.$$

Certainty$_{index}$ is the ratio of the solutions containing the index to the total number of solutions for each product ion structure of the one or more matched metabolized product ion chemical structures. Ratio$_{index}$ is the ratio of the index to total number of indices in each product ion structure of the one or more matched metabolized product ion chemical structures. Specificity$_{product\ ion}$ is the intensity specificity of each product ion structure of the one or more matched metabolized product ion chemical structures. This is calculated according to $$Specificity_{production} = \frac{Intensity_{production}}{\sum Intensity_{production}} \times 100.$$

Intensity$_{product\ ion}$ is the intensity measured by the tandem mass spectrometer for each product ion structure of the one or more matched metabolized product ion chemical structures. ΣIntensity$_{product\ ion}$ is the sum of the intensities measured for all of the one or more matched metabolized product ion chemical structures.

In various embodiments, for each atomic index of the chemical structure of the unmetabolized known compound, processor 940 calculates a modified intensity specificity from the one or more modified matched metabolized product ion chemical structures according to $$Specificity_{index} = \Sigma Ratio_{index} \times Specificity_{product\ ion}.$$

Ratio$_{index}$ is the ratio of the index to total number of indices in each product ion structure of the one or more modified matched metabolized product ion chemical structures. Specificity$_{product\ ion}$ is the intensity specificity of each product ion structure of the one or more modified matched metabolized product ion chemical structures, which is calculated according to $$Specificity_{production} = \frac{Intensity_{production}}{\sum Intensity_{production}} \times 100.$$

Intensity$_{product\ ion}$ is the intensity measured by the tandem mass spectrometer for each product ion structure of the one or more modified matched metabolized product ion chemical structures. ΣIntensity$_{product\ ion}$ is the sum of the intensities measured for all of the one or more modified matched metabolized product ion chemical structures.

In various embodiments, for each atomic index of the chemical structure of the unmetabolized known compound, processor 940 calculates a modified intensity specificity from the one or more modified matched metabolized product ion chemical structures according to $$Specificity_{index} = \Sigma Certainty_{index} \times Ratio_{index} \times Specificity_{product\ ion}.$$

Certainty$_{index}$ is the ratio of the solutions containing the index to the total number of solutions for each product ion structure of the one or more modified matched metabolized product ion chemical structures. Ratio$_{index}$ is the ratio of the index to total number of indices in each product ion structure of the one or more modified matched metabolized product ion chemical structures. Specificity$_{product\ ion}$ is the intensity specificity of each product ion structure of the one or more modified matched metabolized product ion chemical structures, which is calculated according to $$Specificity_{production} = \frac{Intensity_{production}}{\sum Intensity_{production}} \times 100.$$

Intensity$_{product\ ion}$ is the intensity measured by the tandem mass spectrometer for each product ion structure of the one or more modified matched metabolized product ion chemical structures. ΣIntensity$_{product\ ion}$ is the sum of the intensities measured for all of the one or more modified matched metabolized product ion chemical structures.

In various embodiments, for each atomic index of the chemical structure of the unmetabolized known compound, processor 940 calculates a score from the unmodified intensity specificities of the other atomic indices and the modified intensity specificity according to $$Score_{index} = \text{Modified } Specificity_{index} + \sum \text{Unmodified } Specificity_{each\ other\ index}.$$

In various embodiments, for each atomic index of the chemical structure of the unmetabolized known compound, processor 940 calculates a score from the unmodified intensity specificities of the other atomic indices and the modified intensity specificity by performing three steps. First, it divides each unmodified intensity specificity of the other atomic indices by the highest value unmodified intensity specificity. This produces a normalized unmodified intensity specificity for each atomic index. Second, it divides each modified intensity specificity of the other atomic indices by the highest value modified intensity specificity. This produces a normalized modified intensity specificity for each atomic index. Finally, it calculates the score according to $$Score_{index} = \|\text{Modified } Specificity_{index}\| + \sum \|\text{Unmodified } Specificity_{each\ other\ index}\|.$$

In various embodiments, processor 940 further divides each score of each atomic index of the chemical structure of the unmetabolized known compound by the highest score calculated for the atomic indices of the chemical structure of the unmetabolized known compound. This produces a normalized score for each atomic index of the chemical structure of the unmetabolized known compound. It identifies one or more atomic indices of the chemical structure of the unmetabolized known compound with the highest normalized score as one or more sites of modification of the metabolized known compound found in the first sample.

In various embodiments, processor 940 further for each unmatched structure of the one or more unmatched metabolized product ion chemical structures, applies rules for breaking labile bonds of the each unmatched structure to produce one or more chemical modifications to each unmatched structure and compares each unmatched structure and the one or more chemical modifications found to the plurality of unmetabolized product ion chemical structures, producing additional one or more modified matched metabolized product ion chemical structures.

In various embodiments, processor 940 further, before calculating specificities and scores for atomic indices, groups two or more atomic indices into a group index and calculating specificities and scores for the group index like an atomic index.

Method for Identifying Site of Modification

Figure 10:
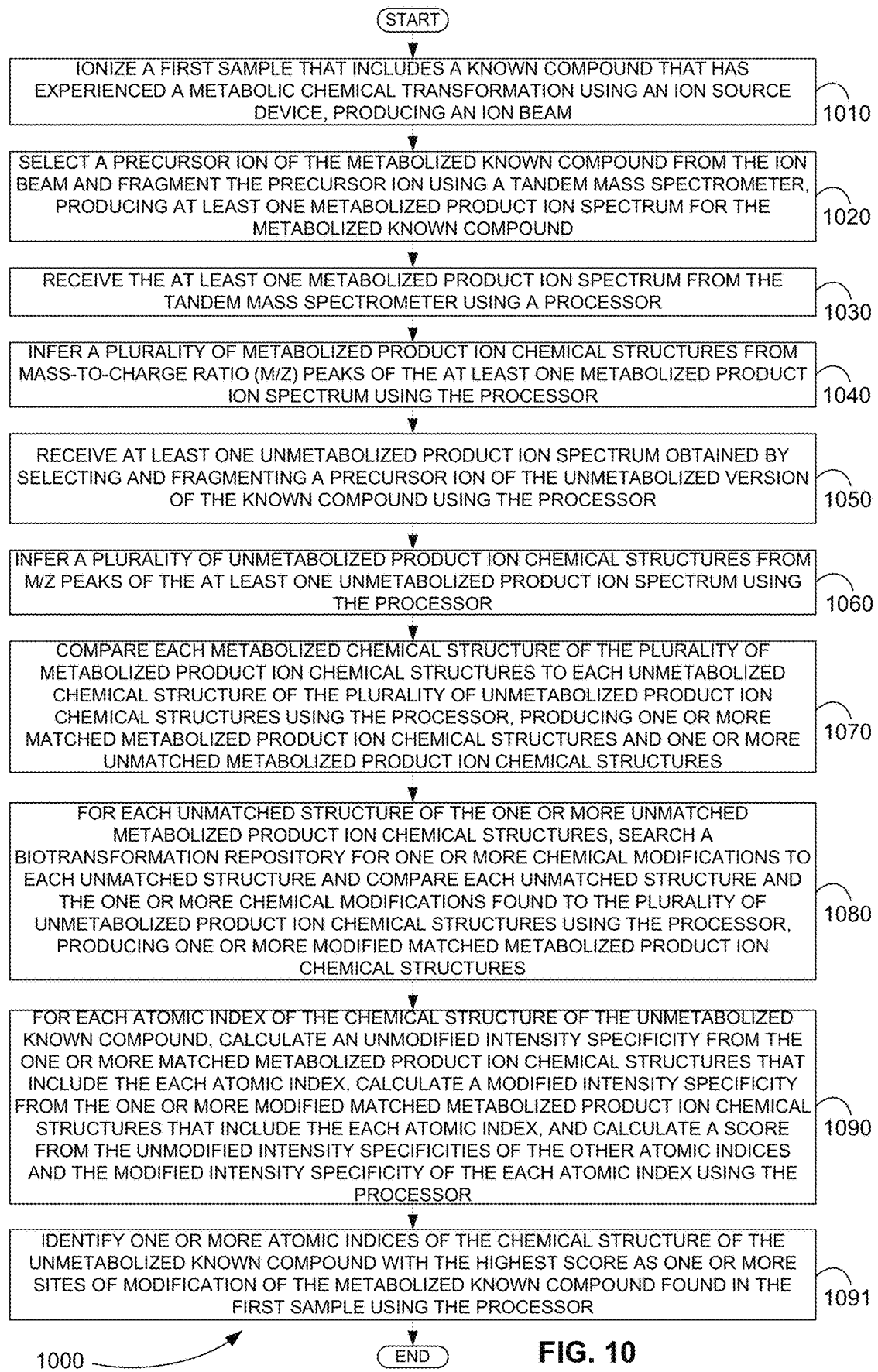
FIG. 10 is a flowchart showing a method for identifying the site of modification of a metabolized known compound using tandem mass spectrometry, in accordance with various embodiments.

FIG. 10 is a flowchart showing a method 1000 for identifying the site of modification of a metabolized known compound using tandem mass spectrometry, in accordance with various embodiments.

In step 1010 of method 1000, a first sample that includes a known compound that has experienced a metabolic chemical transformation is ionized using an ion source device. An ion beam is produced.

In step 1020, a precursor ion of the metabolized known compound is selected from the ion beam and the precursor ion is fragmented using a tandem mass spectrometer. At least one metabolized product ion spectrum is produced for the metabolized known compound.

In step 1030, at least one metabolized product ion spectrum is received from the tandem mass spectrometer using a processor.

In step 1040, a plurality of metabolized product ion chemical structures is inferred from mass-to-charge ratio (m/z) peaks of the at least one metabolized product ion spectrum using the processor.

In step 1050, at least one unmetabolized product ion spectrum is received using the processor. The at least one unmetabolized product ion spectrum is obtained from the first sample or by ionizing a second sample that includes an unmetabolized version of the known compound and selecting and fragmenting a precursor ion of the unmetabolized version of the known compound.

In step 1060, a plurality of unmetabolized product ion chemical structures is inferred from m/z peaks of the at least one unmetabolized product ion spectrum using the processor.

In step 1070, each metabolized chemical structure of the plurality of metabolized product ion chemical structures is compared to each unmetabolized chemical structure of the plurality of unmetabolized product ion chemical structures using the processor. One or more matched metabolized product ion chemical structures and one or more unmatched metabolized product ion chemical structures are produced.

In step 1080, for each unmatched structure of the one or more unmatched metabolized product ion chemical structures, a biotransformation repository is searched for one or more chemical modifications to each unmatched structure and each unmatched structure and the one or more chemical modifications found are compared to the plurality of unmetabolized product ion chemical structures using the processor. One or more modified matched metabolized product ion chemical structures are produced.

In step 1090, for each atomic index of the chemical structure of the unmetabolized known compound, an unmodified intensity specificity is calculated from the one or more matched metabolized product ion chemical structures that include the atomic index, a modified intensity specificity is calculated from the one or more modified matched metabolized product ion chemical structures that include the atomic index, and a score is calculated from the unmodified intensity specificities of the other atomic indices and the modified intensity specificity of the atomic index using the processor.

In step 1091, one or more atomic indices of the chemical structure of the unmetabolized known compound with the highest score are identified as one or more sites of modification of the metabolized known compound found in the first sample using the processor.

Computer Program Product for Identifying Site of Modification

In various embodiments, computer program products include a tangible computer-readable storage medium whose contents include a program with instructions being executed on a processor so as to perform a method for identifying the site of modification of a metabolized known compound using tandem mass spectrometry. This method is performed by a system that includes one or more distinct software modules.

Figure 11:
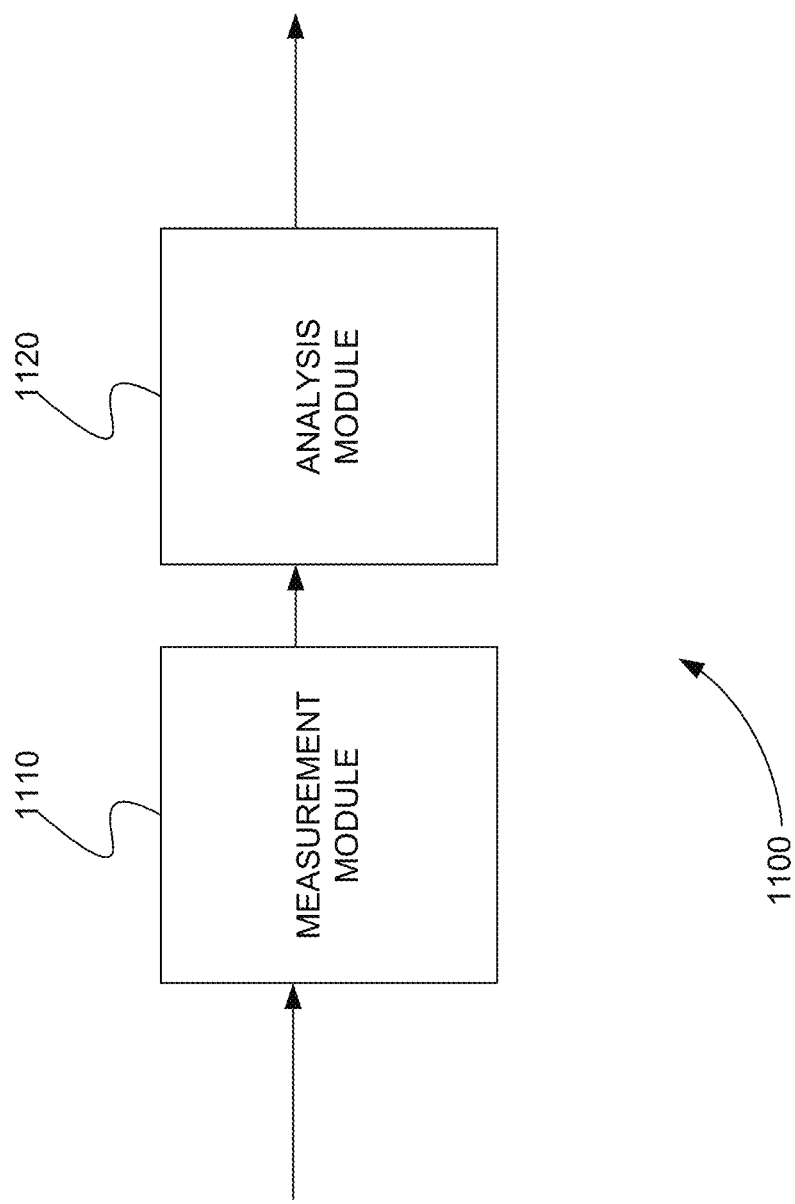
FIG. 11 is a schematic diagram of a system that includes one or more distinct software modules that perform a method for identifying the site of modification of a metabolized known compound using tandem mass spectrometry, in accordance with various embodiments.

FIG. 11 is a schematic diagram of a system 1100 that includes one or more distinct software modules that perform a method for identifying the site of modification of a metabolized known compound using tandem mass spectrometry, in accordance with various embodiments. System 1100 includes measurement module 1110 and analysis modules 1120.

Measurement module 1110 instructs an ion source device to ionize a first sample. The first sample includes a known compound that has experienced a metabolic chemical transformation. An ion beam is produced.

Measurement module 1110 instructs a tandem mass spectrometer to select a precursor ion of the metabolized known compound from the ion beam and fragment the precursor ion. At least one metabolized product ion spectrum is produced for the metabolized known compound.

Analysis module 1120 receives the at least one metabolized product ion spectrum from the tandem mass spectrometer. Analysis module 1120 infers a plurality of metabolized product ion chemical structures from mass-to-charge ratio (m/z) peaks of the at least one metabolized product ion spectrum.

Analysis module 1120 receives at least one unmetabolized product ion spectrum obtained from the first sample or by ionizing a second sample that includes an unmetabolized version of the known compound and selecting and fragmenting a precursor ion of the unmetabolized version of the known compound. Analysis module 1120 infers a plurality of unmetabolized product ion chemical structures from m/z peaks of the at least one unmetabolized product ion spectrum.

Analysis module 1120 compares each metabolized chemical structure of the plurality of metabolized product ion chemical structures to each unmetabolized chemical structure of the plurality of unmetabolized product ion chemical structures. One or more matched metabolized product ion chemical structures and one or more unmatched metabolized product ion chemical structures are produced.

For each unmatched structure of the one or more unmatched metabolized product ion chemical structures, analysis module 1120 searches a biotransformation repository for one or more chemical modifications to each unmatched structure and compares each unmatched structure and the one or more chemical modifications found to the plurality of unmetabolized product ion chemical structures. One or more modified matched metabolized product ion chemical structures are produced.

For each atomic index of the chemical structure of the unmetabolized known compound, analysis module 1120 calculated an unmodified intensity specificity from the one or more matched metabolized product ion chemical structures that include the atomic index, calculated a modified intensity specificity from the one or more modified matched metabolized product ion chemical structures that include the atomic index, and calculated a score from the unmodified intensity specificities of the other atomic indices and the modified intensity specificity of the atomic index.

Analysis module 1120 identifies one or more atomic indices of the chemical structure of the unmetabolized known compound with the highest score as one or more sites of modification of the metabolized known compound found in the first sample.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for identifying the site of modification of a metabolized known compound using tandem mass spectrometry, comprising:
   an ion source device configured to produce an ion beam by ionizing a first sample that includes a known compound that has experienced a metabolic chemical transformation;
   a tandem mass spectrometer configured to produce at least one metabolized product ion spectrum for the metabolized known compound by selecting a precursor ion of the metabolized known compound from the ion beam and fragmenting the precursor ion;
   a processor in communication with the tandem mass spectrometer that receives the at least one metabolized product ion spectrum,
      infers a plurality of metabolized product ion chemical structures from mass-to-charge ratio (m/z) peaks of the at least one metabolized product ion spectrum,
      receives at least one unmetabolized product ion spectrum obtained by selecting and fragmenting a precursor ion of the unmetabolized version of the known compound,
      infers a plurality of unmetabolized product ion chemical structures from m/z peaks of the at least one unmetabolized product ion spectrum,
      compares each metabolized chemical structure of the plurality of metabolized product ion chemical structures to each unmetabolized chemical structure of the plurality of unmetabolized product ion chemical structures, producing one or more matched metabolized product ion chemical structures and one or more unmatched metabolized product ion chemical structures,
      for each unmatched structure of the one or more unmatched metabolized product ion chemical structures, searches a biotransformation repository for one or more chemical modifications to each unmatched structure and compares each unmatched structure and the one or more chemical modifications found to the plurality of unmetabolized product ion chemical structures, producing one or more modified matched metabolized product ion chemical structures,
      for each atomic index of the chemical structure of the unmetabolized known compound, calculates an unmodified intensity specificity from the one or more matched metabolized product ion chemical structures that include the each atomic index, calculates a modified intensity specificity from the one or more modified matched metabolized product ion chemical structures that include the each atomic index, and calculates a score from the unmodified intensity specificities of the other atomic indices and the modified intensity specificity of the each atomic index, wherein the processor for each atomic index of the chemical structure of the unmetabolized known compound, calculates an unmodified intensity specificity from the one or more matched metabolized product ion chemical structures according to $$Specificity_{index} = \Sigma Ratio_{index} \times Specificity_{product\ ion}$$

where $Ratio_{index}$ is the ratio of the index to total number of indices in each product ion structure of the one or more matched metabolized product ion chemical structures and $Specificity_{product\ ion}$ is the intensity specificity of each product ion structure of the one or more matched metabolized product ion chemical structures, which is calculated according to $$Specificity_{production} = \frac{Intensity_{production}}{\sum Intensity_{production}} \times 100$$

where $Intensity_{product\ ion}$ is the intensity measured by the tandem mass spectrometer for each product ion structure of the one or more matched metabolized product ion chemical structures and $\Sigma Intensity_{product\ ion}$ is the sum of the intensities measured for all of the one or more matched metabolized product ion chemical structures, and
   identifies one or more atomic indices of the chemical structure of the unmetabolized known compound with the highest score as one or more sites of modification of the metabolized known compound found in the first sample.

2. A system for identifying the site of modification of a metabolized known compound using tandem mass spectrometry, comprising:
   an ion source device configured to produce an ion beam by ionizing a first sample that includes a known compound that has experienced a metabolic chemical transformation;
   a tandem mass spectrometer configured to produce at least one metabolized product ion spectrum for the metabolized known compound by selecting a precursor ion of the metabolized known compound from the ion beam and fragmenting the precursor ion;

a processor in communication with the tandem mass spectrometer that receives the at least one metabolized product ion spectrum, infers a plurality of metabolized product ion chemical structures from mass-to-charge ratio (m/z) peaks of the at least one metabolized product ion spectrum, receives at least one unmetabolized product ion spectrum obtained by selecting and fragmenting a precursor ion of the unmetabolized version of the known compound, infers a plurality of unmetabolized product ion chemical structures from m/z peaks of the at least one unmetabolized product ion spectrum, compares each metabolized chemical structure of the plurality of metabolized product ion chemical structures to each unmetabolized chemical structure of the plurality of unmetabolized product ion chemical structures, producing one or more matched metabolized product ion chemical structures and one or more unmatched metabolized product ion chemical structures, for each unmatched structure of the one or more unmatched metabolized product ion chemical structures, searches a biotransformation repository for one or more chemical modifications to each unmatched structure and compares each unmatched structure and the one or more chemical modifications found to the plurality of unmetabolized product ion chemical structures, producing one or more modified matched metabolized product ion chemical structures, for each atomic index of the chemical structure of the unmetabolized known compound, calculates an unmodified intensity specificity from the one or more matched metabolized product ion chemical structures that include the each atomic index, calculates a modified intensity specificity from the one or more modified matched metabolized product ion chemical structures that include the each atomic index, and calculates a score from the unmodified intensity specificities of the other atomic indices and the modified intensity specificity of the each atomic index, divides each score of each atomic index of the chemical structure of the unmetabolized known compound by the highest score calculated for the atomic indices of the chemical structure of the unmetabolized known compound, producing a normalized score for each atomic index of the chemical structure of the unmetabolized known compound, and identifies one or more atomic indices of the chemical structure of the unmetabolized known compound with the highest normalized score as one or more sites of modification of the metabolized known compound found in the first sample.

3. A computer program product, comprising a non-transitory tangible computer-readable storage medium whose contents include a program with instructions being executed on a processor so as to perform a method for identifying the site of modification of a metabolized known compound using tandem mass spectrometry, comprising:

providing a system, wherein the system comprises one or more distinct software modules, and wherein the distinct software modules comprise a measurement module and an analysis module;

instructing an ion source device to produce an ion beam by ionizing a first sample that includes a known compound that has experienced a metabolic chemical transformation using the measurement module;

instructing a tandem mass spectrometer to produce at least one metabolized product ion spectrum for the metabolized known compound by selecting a precursor ion of the metabolized known compound from the ion beam and fragmenting the precursor ion using the measurement module;

receiving the at least one metabolized product ion spectrum from the tandem mass spectrometer using the analysis module;

inferring a plurality of metabolized product ion chemical structures from mass-to-charge ratio (m/z) peaks of the at least one metabolized product ion spectrum using the analysis module;

receiving at least one unmetabolized product ion spectrum obtained by selecting and fragmenting a precursor ion of the unmetabolized version of the known compound using the analysis module;

inferring a plurality of unmetabolized product ion chemical structures from m/z peaks of the at least one unmetabolized product ion spectrum using the analysis module;

comparing each metabolized chemical structure of the plurality of metabolized product ion chemical structures to each unmetabolized chemical structure of the plurality of unmetabolized product ion chemical structures using the analysis module, producing one or more matched metabolized product ion chemical structures and one or more unmatched metabolized product ion chemical structures, for each unmatched structure of the one or more unmatched metabolized product ion chemical structures, searching a biotransformation repository for one or more chemical modifications to each unmatched structure and comparing each unmatched structure and the one or more chemical modifications found to the plurality of unmetabolized product ion chemical structures using the analysis module, producing one or more modified matched metabolized product ion chemical structures, for each atomic index of the chemical structure of the unmetabolized known compound, calculating an unmodified intensity specificity from the one or more matched metabolized product ion chemical structures that include the each atomic index, calculating a modified intensity specificity from the one or more modified matched metabolized product ion chemical structures that include the each atomic index, and calculating a score from the unmodified intensity specificities of the other atomic indices and the modified intensity specificity of the each atomic index using the analysis module, dividing each score of each atomic index of the chemical structure of the unmetabolized known compound by the highest score calculated for the atomic indices of the chemical structure of the unmetabolized known compound, producing a normalized score for each atomic index of the chemical structure of the unmetabolized known compound, and identifying one or more atomic indices of the chemical structure of the unmetabolized known compound with the highest normalized score as one or more sites of modification of the metabolized known compound found in the first sample using the analysis module.

\* \* \* \* \*